(12) United States Patent
Gaw et al.

(10) Patent No.: US 8,420,055 B2
(45) Date of Patent: Apr. 16, 2013

(54) AMINE FUNCTIONALIZED SUPERPARAMAGNETIC NANOPARTICLES FOR THE SYNTHESIS OF BIOCONJUGATES AND USES THEREFOR

(75) Inventors: Debra A. Gaw, Reading, MA (US); Lee Josephson, Reading, MA (US)

(73) Assignee: VisEn Medical, Inc., Waltham, MA (US)

( * ) Notice: Subject to any disclaimer, the term of this patent is extended or adjusted under 35 U.S.C. 154(b) by 1233 days.

(21) Appl. No.: 12/118,020

(22) Filed: May 9, 2008

(65) Prior Publication Data
US 2009/0068115 A1   Mar. 12, 2009

Related U.S. Application Data

(63) Continuation of application No. 10/335,790, filed on Jan. 2, 2003, now abandoned.

(60) Provisional application No. 60/345,233, filed on Jan. 2, 2002.

(51) Int. Cl.
*A61K 49/18* (2006.01)

(52) U.S. Cl.
USPC ............... 424/9.34; 424/9.35; 252/62.53

(58) Field of Classification Search ............ 424/9.34
See application file for complete search history.

(56) References Cited

U.S. PATENT DOCUMENTS

| | | | |
|---|---|---|---|
| 4,101,435 A | 7/1978 | Hasegawa et al. | |
| 4,219,335 A | 8/1980 | Ebersole | |
| 4,369,226 A | 1/1983 | Rembaum | |
| 4,438,239 A | 3/1984 | Rembaum et al. | |
| 4,452,773 A | 6/1984 | Molday | |
| 4,628,037 A | 12/1986 | Chagnon et al. | |
| 4,654,267 A | 3/1987 | Ugelstad et al. | |
| 4,981,977 A | 1/1991 | Southwick et al. | |
| 5,164,297 A | 11/1992 | Josephson et al. | |
| 5,204,457 A | 4/1993 | Maruno et al. | |
| 5,262,176 A | 11/1993 | Palmacci et al. | |
| 5,268,486 A | 12/1993 | Waggoner et al. | |
| 5,395,688 A | 3/1995 | Wang et al. | |
| 5,424,419 A | 6/1995 | Hasegawa et al. | |

(Continued)

FOREIGN PATENT DOCUMENTS

| CA | 2384429 A1 | 3/2001 |
|---|---|---|
| EP | 1065250 | 1/2001 |

(Continued)

OTHER PUBLICATIONS

Examination Report of the European Patent Office for EP 03705645.4, dated Sep. 25, 2007, 3 pages.

(Continued)

*Primary Examiner* — Jake M. Vu
(74) *Attorney, Agent, or Firm* — Goodwin Procter LLP

(57) ABSTRACT

Amine functionalized magnetic nanoparticle compositions and processes for synthesizing the same are described. The process consists of obtaining a carboxylated polymer in substantially pure form, which is used to prepare a substantially size homogeneous, polymer coated carboxyl, functionalized magnetic nanoparticle. The carboxyl groups are converted to reactive primary amino groups by the use of a water-soluble carbodiimide followed by reaction of a large excess of a diamine. The amine-terminated nanoparticles are then reacted with bifunctional crosslinking agents and with various biomolecules to make nanoparticles for in vitro assays, cell sorting applications and target specific MR contrast agents.

8 Claims, 2 Drawing Sheets

U.S. PATENT DOCUMENTS

| | | |
|---|---|---|
| 5,445,970 A | 8/1995 | Rohr |
| 5,478,576 A | 12/1995 | Jung et al. |
| 5,486,616 A | 1/1996 | Waggoner et al. |
| 5,512,439 A | 4/1996 | Hornes et al. |
| 5,539,658 A | 7/1996 | McCullough |
| 5,569,587 A | 10/1996 | Waggoner |
| 5,569,766 A | 10/1996 | Waggoner et al. |
| 5,593,658 A | 1/1997 | Bogdanov et al. |
| 5,627,027 A | 5/1997 | Waggoner |
| 5,808,044 A | 9/1998 | Brush et al. |
| 5,877,310 A | 3/1999 | Reddington et al. |
| 5,981,507 A | 11/1999 | Josephson et al. |
| 6,002,003 A | 12/1999 | Shen et al. |
| 6,004,536 A | 12/1999 | Leung et al. |
| 6,008,373 A | 12/1999 | Waggoner et al. |
| 6,043,025 A | 3/2000 | Minden et al. |
| 6,046,585 A | 4/2000 | Simmonds |
| 6,074,884 A | 6/2000 | Siiman et al. |
| 6,083,486 A | 7/2000 | Weissleder et al. |
| 6,120,856 A | 9/2000 | Liberti et al. |
| 6,127,134 A | 10/2000 | Minden et al. |
| 6,130,094 A | 10/2000 | Waggoner et al. |
| 6,133,047 A | 10/2000 | Elaissari et al. |
| 6,133,445 A | 10/2000 | Waggoner et al. |
| 6,136,612 A | 10/2000 | Della Ciana et al. |
| 6,248,539 B1 | 6/2001 | Ghadiri et al. |
| 6,274,121 B1 | 8/2001 | Pilgrimm |
| 6,275,031 B1 | 8/2001 | Simmonds |
| 6,448,008 B1 | 9/2002 | Caputo et al. |
| 6,503,762 B1 | 1/2003 | Yamauchi et al. |
| 6,548,264 B1 | 4/2003 | Tan et al. |
| 6,592,847 B1 | 7/2003 | Weissleder et al. |
| 6,615,063 B1 | 9/2003 | Ntziachristos et al. |
| 6,720,177 B2 | 4/2004 | Ghadiri et al. |
| 6,720,351 B2 | 4/2004 | Bertinato et al. |
| 6,734,000 B2 | 5/2004 | Chin et al. |
| 6,740,755 B2 | 5/2004 | Caputo et al. |
| 6,747,159 B2 | 6/2004 | Caputo et al. |
| 6,767,635 B1 | 7/2004 | Bahr et al. |
| 6,949,572 B2 | 9/2005 | Bertinato et al. |
| 2003/0092029 A1 | 5/2003 | Josephson et al. |
| 2003/0124194 A1 | 7/2003 | Gaw et al. |
| 2003/0206859 A1 | 11/2003 | Chen et al. |
| 2005/0130167 A1 | 6/2005 | Bao et al. |
| 2005/0169843 A1 | 8/2005 | Weissleder et al. |
| 2005/0171434 A1 | 8/2005 | Madden et al. |
| 2005/0214221 A1 | 9/2005 | Poss et al. |
| 2006/0169843 A1 | 8/2006 | Barrs et al. |
| 2006/0275775 A1 | 12/2006 | Weissleder et al. |
| 2008/0102036 A1 | 5/2008 | Poss et al. |
| 2008/0226562 A1 | 9/2008 | Groves et al. |
| 2009/0068115 A1 | 3/2009 | Gaw et al. |

FOREIGN PATENT DOCUMENTS

| | | |
|---|---|---|
| EP | 1787659 A1 | 5/2007 |
| EP | 1787661 A1 | 5/2007 |
| WO | WO-97/21452 A2 | 6/1997 |
| WO | WO-97/40104 | 10/1997 |
| WO | WO-99/51702 | 10/1999 |
| WO | WO-00/61191 A2 | 10/2000 |
| WO | WO-01/19405 A2 | 3/2001 |
| WO | WO-01/20338 A1 | 3/2001 |
| WO | WO-01/21624 | 3/2001 |
| WO | WO-02/098364 A2 | 12/2002 |
| WO | WO-03/007579 A2 | 1/2003 |
| WO | WO-03/057175 A2 | 7/2003 |
| WO | WO-03/079015 | 9/2003 |
| WO | WO-03/102558 A1 | 12/2003 |
| WO | WO-2004/026344 A1 | 4/2004 |
| WO | WO-2004/083902 | 9/2004 |
| WO | WO-2004/108902 | 12/2004 |
| WO | WO-2005/017539 | 2/2005 |
| WO | WO-2006/010083 A2 | 1/2006 |
| WO | WO-2006/028129 A1 | 3/2006 |
| WO | WO-2007/021946 A2 | 2/2007 |
| WO | WO-2007/028037 | 3/2007 |
| WO | WO-2007/028118 | 3/2007 |
| WO | WO-2007/028163 | 3/2007 |
| WO | WO-2007/136413 | 11/2007 |

OTHER PUBLICATIONS

Examination Report of the European Patent Office for EP 03705645.4, dated May 25, 2009, 4 pages.
Goetze et al. (2002) "Biocompatible Magnetic Core/Shell Nanoparticles," *Journal of Magnetism and Magnetic Materials*, 252: 399-402.
Hogemann et al. (2000) "Improvement of MRI Probes to Allow Efficient Detection of Gene Expression," *Bioconjugate Chem.*, 11: 941-946.
International Preliminary Examination Report for PCT/US2003/000051, dated Nov. 28, 2003, 3 pages.
International Search Report of the International Searching Authority for PCT/US2003/000051 dated Jul. 29, 2003, 1 page.
Josephson et al. (1996) "Antiviral Activity of a Conjugate of Adenine-9-β-D-Arabinofuranoside 5'-Monophosphate and a 9 kDa Fragment of Arabinogalactan," *Antiviral Therapy*, 1: 147-156.
Josephson et al. (1999) "High-Efficiency Intracellular Magnetic Labeling with Novel Superparamagnetic-Tat Peptide Conjugates," *Bioconjugate Chem.*, 10: 186-191.
Josephson et al. (2001) "Magnetic Nanosensors for the Detection of Oligonucleotide Sequences," *Angew. Chem. Int. Ed.*, 40: 3204-3206.
Kreuter (1996) "Nanoparticles and microparticles for drug and vaccine delivery," *Journal of Anatomy*, 189: 503-505.
Pardoe et al. (2001) "Structural and magnetic properties of nanoscale iron oxide particles synthesized in the presence of dextran or polyvinol alcohol," *Journal of Magnetism and Magnetic Materials*, 245: 41-46.
Satomura et al. (1984) "Kinetics of human pancreatic and salivary alpha-amylases with carboxymethylamyloses as substrates," *Clinica Chimica Acta*, 138: 21-29.
Schutt et al. (1997) "Applications of magnetic targeting in diagnosis and therapy—possibilities and limitations: a mini-review," *Hybridoma*, 16: 109-117.
Summons to attend oral proceedings issued by the European Patent Office for EP 03705645.4, dated Mar. 4, 2011, 5 pages.
Supplementary Partial European Search Report for EP 03705645.4, PCT/2003/000051, dated Jun. 8, 2006, 4 pages.
Achilefu et al. (2000) "Novel Receptor-Targeted Fluorescent Contrast Agents for In Vivo Tumor Imaging," *Invest. Radiol.* 35:479-485.
Alauddin et al. (2003) "Receptor Mediated Uptake of a Radiolabeled Contrast Agent Sensitive to Beta-Galectosidase Activity," *Nuclear Medicine and Biology* 30:261-265.
Alfano et al. (1997) "Advances in optical imaging of biomedical media," *Ann. NY Acad. Sci.* 820:248-271.
Allen et al. (2004) "Magnetic Resonance Contrast Agents for Medical and Molecular Imaging," *Metal Ions Biol. Syst.* 42:1-38.
Ballou et al. (1997) "Tumor Detection and Visualization Using Cyanine Fluorochrome-Labeled Antibodies," *Biotechnol. Prog.* 13:649-658.
Banks et al. (1995) "Comparison of three common amine reactive fluorescent probes used for conjugation to biomolecules by capillary zone electrophoresis," *Bioconjug. Chem.* 6:447-458.
Becker et al. (2001) "Receptor-Targeted Optical Imaging of Tumors with Near-Infrared Fluorescent Ligands," *Nature Biotech.* 19:327-331.
Bremer et al. (2001) "In Vivo Molecular Target Assessment of Matrix Metalloproteinase Inhibition," *Nature Med.* 7:743-748.
Brigger et al. (2002) "Nanoparticles in Cancer Therapy and Diagnosis," *Advanced Drug Delivery Reviews* 54: 631-651.
Bugai et al. (2001) "Novel Fluorescent Contract Agents for Optical Imaging of in vivo Tumor Based on a Receptor-Target Dye-Peptide Conjugate Platform," *J. Biomed. Opt.* 6:122-133.
Chemla et al. (2000) "Ultrasensitive Magnetic Biosensor for Homogeneous Immunoassay," *PNAS* 97: 14268-14272.
Chen et al. (2003) "Sodium Chloride Modified Silica Nanoparticles as a Non-Viral Vector with a High Efficiency of DNA Transfer into Cells," *Current Gene Therapy* 3: 273-279.

Cunin et al. (2002) "Biomolecular Screening with Encoded Porous-Silicon Photonic Crystals," *Nature Materials* 1:39-41.
Delie et al. (2005) "Polymeric Particulates to Improve Oral Bioavailability of Peptide Drugs," *Molecules* 10: 65-80.
Derfus et al. (2004) "Probing the Cytoxicity of Semiconductor Quantum Dots," *Nano Lett.* 4:11-18.
Eliyahu et al. (2005) "Polymers for DNA Delivery," *Molecules* 10: 24-64.
Frangioni (2003) "In vivo near-infrared fluorescence imaging," *Curr. Opin. Chem. Biol.* 7(5):626-634.
Gupta et al. (2005) "Synthesis and Surface Engineering of Iron Oxide Nanoparticles for Biomedical Applications," *Biomaterials* 26:3995-4021.
Högemann et al. (2002) "High Throughput Magnetic Resonance Imaging for Evaluating Targeted Nanoparticle Probes," *Bioconjugate Chem.* 13(1):116-121.
Hüber et al. (1998) "Fluorescently Detectable Magnetic Resonance Imaging Agents," *Bioconjugate Chem.* 9(2):242-249.
International Search Report of the International Searching Authority for PCT/US2006/049222 dated Sep. 8, 2008, 10 pages.
Jaffer et al. (2006) "Molecular imaging of myocardial infarction " *J. Mol. Cell. Cardiology* 41(6):921-933.
Josephson et al. (2002) "Near-infrared fluorescent nanoparticles as combined MR/optical imaging probes," *Bioconjugate Chem.* 13(3):554-560.
Kim et al. (2003) "Type-II Quantum Dots: CdTe/CdSe(core/shell) and CdSe/ZnTe(core/shell) Heterostructures," *J. Am. Chem. Soc.* 125:11466-11467.
Kircher et al. (2003) "A multimodal nanoparticle for preoperative magnetic resonance imaging and intraoperative optical brain tumor delineation," *Cancer Research* 63:8122-8125.
Kircher et al. (2004) "A Dual Fluorochrome Probe for Imaging Proteases " *Bioconjugate Chem.* 15: 242-248.
Koo et al. (2006) "Brain cancer diagnosis and therapy with nanoplatforms " *Adv. Drug Delivery Reviews* 58(14):1556-1577.
Leamon et al. (2001) "Folate-Mediated Targeting: From Disgnostics to Drug and Gene Delivery," *Drug Discovery Today* 1(6):44-51.
McNeil, S. (2005) "Nanotechnology for the Biologist " *Journal of Leukocyte Biology* 78:585-594.
Meade et al. (2003) "New Magnetic Resonance Contract Agents as Biochemical Reporters," *Curr Opin Neurobiol.* 13(5):597-602.
Medarova et al. (2005) "In vivo imaging of tumor response to therapy using a dual-modality imaging strategy," *Int. J. Cancer* 118(11):2796-2802.
Mohanraj et al. (2006) "Nanoparticles—A Review " *Tropical Journal of Pharmaceutical Research* 5(1): 561-573.
Neri et al. (1997) "Targeting by Affinity-Matured Recombinant Antibody Fragments of an Angiogenesis Associated Fibronectin Isoform," *Nature Biotech.* 15:1271-1275.
Ntziachristos et al. (2000) "Concurrent MRI and Diffuse Optical Tomography of Breast After Indocyanine Green Enhancement," *PNAS* 97: 2767-2772.
Ozmen et al. (2000) "Infrared fluorescence sensing of submicromolar calcium: pushing the limits of photoinduced electron transfer," *Tetrahedron Letters*, 41:9185-9188.
Park et al. (2005) "Biodegradable Polymers for Microencapsulation of Drugs " *Molecules* 10: 146-161.
Pinaud et al. (2006) "Advances in Fluorescence Imaging with Quantum Dot Bio-probes," *Biomaterials* 27(9): 1679-1687.
Qhobosheane et al. (2001) "Biochemically Functionalized Silica Nanoparticles " *Analyst* 126: 1274-1278.
Reynolds et al. (1977) "Stable Heptamethine Pyrylium Dyes that Absorb in the Infrared," *J. Org. Chem.* 22(5):885-888.
Reynolds et al. (2005) "Protamine as an Efficient Membrance-Translocating Peptide," *Bioconjugate Chem.* 16(5):1240-1245.
Santra et al. (2001) "Conjugation of Biomolecules with Luminophore-Doped Silica Nanoparticles for Photostable Biomarkers," *Analytical Chemistry* 73(20):4988-4993.
Schellenberger et al. (2004) "Magneto/Optical Annexin V, a Multimodal Protein " *Bioconjugate Chemistry* 15:1062-1067.
Sun et al. (2006) ""Clickable" Nanoparticles for Targeted Imaging," *Mol. Imaging* 5(2):122-128.
Tearney et al. (1996) "Catheter-Based Optical Imaging of a Human Coronary Artery," *Circulation* 94:3013.
Tsourkas et al. (2005) "In Vivo imaging of activated endothelium using an anti-VCAM-1 magnetooptical probe," *Bioconjugate Chem.* 16(3): 576-581.
Tyagi et al. (1998) "Multicolor Molecular Beacons for Allele Discrimination," *Nat. Biotechnol.* 16:49-53.
Tyagi et al. (2000) "Wavelength-Shifting Molecular Beacons," *Nat. Biotechnol.* 18:1191-1196.
van Kerkhof et al. (1995) "The ISFET based heparin sensor with a monolayer of protamine as affinity ligand," *Biosens Bioelectron.* 10:269-282.
Veiseh et al. (2005) "Optical and MRI multifunctional nanoprobe for targeting gliomas," *Nano Letters* 5(6):1003-1008.
Weissleder et al. (1999) "In vivo imaging of tumors with protease-activated near-infrared fluorescent probes," *Nature Biotech.* 17:375-378.
Winter et al. (2003) "Molecular Imaging of Angiogenesis in Early-Stage Artheroscleросis With $\alpha_v\beta_3$-Integrin-Targeted Nanoparticles," *Circulation* 108:2270-2274.
Winter et al. (2003) "Molecular Imaging of Angiogenesis in Nascent Vx-2 Rabbit Tumors Using a Novel $\alpha_v\beta_b$-targeted Nanoparticle and 1.5 Tesla Magnetic Resonance Imaging," *Cancer Research* 63:5838-5843.
Written Opinion of the International Searching Authority for PCT/US2006/049222, dated Sep. 8, 2008, 10 pages.
Wunderbaldinger et al. (2002) "Tat Peptide Directs Enhanced Clearance and Hepatic Permeability of Magnetic Nanoparticles " *Bioconjugate Chem.* 13(2):264-268.
Xu et al. (2003) "Room-temperature preparation and characterization of poly (ethylene glycol)-coated silica nanoparticles for biomedical applications " *J. Biomed. Mater. Res. A.* 66(4):870-879.
Yih et al. (2006) "Engineered Nanoparticles as Precise Drug Delivery Systems " *Journal of Cellular Biochemistry* 97: 1184-1190.
Zhang et al. (2005) "Gadolinium Meets Medicinal Chemistry: MRI Contrast Agent Development," *Curr. Med. Chem.* 12(7):751-778.

US 8,420,055 B2

AMINE FUNCTIONALIZED SUPERPARAMAGNETIC NANOPARTICLES FOR THE SYNTHESIS OF BIOCONJUGATES AND USES THEREFOR

RELATED APPLICATIONS

This Application is a continuation of U.S. patent application Ser. No. 10/335,790, filed Jan. 2, 2003, which claims the benefit of and priority under 35 U.S.C. §119(e) to U.S. provisional patent application Ser. No. 60/345,233 filed Jan. 2, 2002, the entire contents of each of these applications are hereby incorporated by reference.

TECHNICAL FIELD

The present invention relates to novel superparamagnetic nanoparticle compositions, synthesis and uses thereof.

BACKGROUND

All patents, patent applications and references cited in this specification are incorporated herein by reference.

Carboxyl bearing polymers have found a wide usage in food, drugs, and industrial applications. A few well known examples include the carboxymethyl ('CM') polysaccharides CM-cellulose, CM-dextran, and CM-arabinogalactan (U.S. Pat. No. 5,981,507). The CM polysaccharides are produced from a reaction of the polysaccharide with haloacetic acids in base.

Carboxyl bearing polymers have been used in the synthesis of magnetic nanoparticles. Carboxylated dextrans of two major types have been used in the synthesis of superparamagnetic iron oxide nanoparticles. Carboxydextrans have a single terminal carboxyl group on each dextran molecule obtained by treatment with base (Hasegawa U.S. Pat. No. 4,101,435; Hasegawa U.S. Pat. No. 5,424,419, column 2, line 17). Carboxymethylated dextrans have numerous carboxymethyl groups attached per mole of dextran by reaction of alkyl halogenated acids in base (Maruno U.S. Pat. No. 5,204,457; Groman WO 00/61191).

Magnetic nanoparticles used for the attachment of biomolecules have been described by Molday (U.S. Pat. No. 4,452, 773). A dextran coated magnetic nanoparticle is formed and then treated with periodate to produce aldehyde groups. The aldehydes react with amino groups on a biological molecule, to form a Schiff base. The Schiff base maybe stabilized by treatment of with a reducing agent like sodium borohydride. After treatment with a reducing agent a methylene amino linker connects the biomolecule to the nanoparticle. As shown in FIG. 2B, there are no peptidyl bonds in such linkages. A drawback of this method is the difficulty controlling the number and position of amino groups on the biomolecule that are available to react with the reactive aldehyde groups on the nanoparticle.

Other methods of attaching biomolecules to nanoparticles also use the reactivity of the aldehyde group. Rembaum and coworkers have utilized this approach, synthesizing nanoparticles with glutaraldehyde (U.S. Pat. No. 4,438,239; U.S. Pat. No. 4,369,226).

The development of amine functionalized crosslinked iron oxide nanoparticle ("amino-CLIO", FIG. 2) by one of the inventors has proven to be an excellent method of synthesizing magnetic particle-biomolecule conjugates. Amino-CLIO is prepared by first synthesizing a dextran coated magnetic nanoparticle, followed by crosslinking the dextran with epichlorohydrin. Finally the amine groups are incorporated by reacting the dextran with ammonia (see Josephson et al, (1999) Bioconjug Chem 10, 186-91; Josephson et. al (2001) Angwandte Chemie 40, 3204-3206).

Amino-CLIO is an excellent label for the attachment of biomolecules, and for the synthesis of magnetic nanoparticle-biomolecule conjugates, for two reasons. First it provides an amine group for reaction with many bifunctional conjugation reagents that consist of N-hydroxysuccinimide esters that react first with an amine group and have a second group that reacts with sulfhydryl groups on a biomolecule. Examples of these bifunctional conjugating reagents are SPDP, SIA, SMCC and MBS. These reagents are available commercially (Pierce Chemical or Molecular Biosciences). Examples of biomolecules that have been attached to amino-CLIO include peptides (Josephson et al, (1999) Bioconjug Chem 10, 186-91), oligonucleotides (Josephson et. al (2001) Angwandte Chemie 40, 3204-3206) and proteins (Hogemann et al. (2000). Bioconjug Chem 11, 941-6). Second, amino-CLIO is highly stable due to the fact that the crosslinking forms a shell of dextran around a core of iron oxide. This allows storage of either amino-CLIO or bioconjugates based on amino-CLIO under a wide range of conditions (temperature, pH, ionic strength). By covalently joining polymeric molecules of the coating, crosslinking is associated with a pronounced increase in the molecular weight of the polymeric coating.

This amino-CLIO based chemistry has one major drawback, however, which arises precisely because of the extraordinary stability achieved by using a crosslinked-stabilized dextran on the nanoparticle surface. For human parenteral applications, such as for a magnetic label for targeted MR contrast agents, the degradation or elimination of the agent, including the coating, is required. However, when the iron oxide of an amino-CLIO based MR contrast is dissolved or biodegraded, the crosslinked dextran remains as a non-degradable sphere of polysaccharide. Similarly, non-degradability occurs with micron-sized magnetic microspheres where iron oxide is entrapped in a non-biodegradable polymeric shell (see U.S. Pat. No. 4,654,267; U.S. Pat. No. 5,512, 439).

CM-polymers can also function as starting materials for the synthesis of drugs conjugates or for the attachment of various biological molecules. As drug conjugates, CM-arabinogalactan, CM-dextran and polyvinyl alcohol were used as carriers for nucleotide analogues (U.S. Pat. No. 5,981, 507). The carboxyl groups were converted to primary amino groups by reaction with diamines. Biological molecules like araAMP were then attached to the primary amine of the aminated arabinogalactan, see Josephson, et al. (1996) Antivir Ther 1, 147-56 and U.S. Pat. No. 5,478,576.

In these examples, the CM-polymers, such as CM-arabinogalactan, exist as macromolecules in solution, which allows conditions to be employed that insure the nearly quantitative conversion of carboxyl groups to amino groups. The absence of protected carboxyl groups allows essentially all carboxyl groups to be chemically reactive.

There is a need for a improved magnetic nanoparticles to which biomolecules can be attached for use in cell sorting applications, in vitro assays, and which can be used as an intravenously administerable, MR contrast agents. The ideal nanoparticle must have a surface chemistry amenable to the efficient attachment of biomolecules with retention of their biological activity. It must be highly stable in vitro, both before and after the attachment of biomolecules. Yet it must be labile or degradable in vivo, with the utilization or elimination of all of its components.

SUMMARY

The present invention relates to aminofunctionalized nanoparticles. In one embodiment, the nanoparticles have a magnetic core having one or more magnetic metal oxide crystals, and a noncrosslinked polymer coating associated with the core. The polymer coating has a plurality of carboxyl groups and plurality of reactive primary amino groups. A portion of the carboxyl groups are associated with the crystals. In one embodiment, a portion of the amino groups are associated with polymer through a peptidyl linkage of the formula:

wherein X is $-(CH_2)_nNH_2$, $-(CH_2)_oCH\ NHCOO-$, $-(CH_2)_3NH(CH_2)_4NH_2$ or $-(CH_2)_3NH(CH_2)_4NH(CH_2)_3NH_2-$ wherein m=1, 2, or 3; n=2, 3, 6, and o=3 or 4.

In one embodiment, the magnetic core has one or more superparamagnetic iron oxide crystals. The superparamagnetic core has a diameter between about 1 nm and about 25 nm, preferably between about 3 nm and about 10 nm, and more preferably about 5 nm.

The nanoparticle (core and polymer) has diameter between about 15 nm and 100 nm, preferably between about 20 nm and about 100 nm.

The polymer coating may be made from natural polymers, or synthetic polymers, or derivatives or each. Nonlimiting examples include polyvinyl alcohol and carboxymethyldextran In one aspect of the invention, the nanoparticle can be conjugated to a biomolecule.

In another aspect of the invention, there is provided a nanoparticle biomolecule conjugate. The nanoparticle portion includes a magnetic core having one or more magnetic metal oxide crystals, a noncrosslinked polymer coating associated with the core. As in the previous embodiment, the polymer coating has a plurality of carboxyl groups and plurality of reactive primary amino groups. A portion of the carboxyl groups are associated with the crystals, In one embodiment, the amino groups are associated with polymer through a peptidyl linkage of the formula:

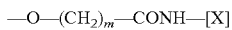

wherein X is $-(CH_2)_nNH_2$, $-(CH_2)_oCH\ NHCOO-$, $-(CH_2)_3NH(CH_2)_4NH_2$ or $-(CH_2)_3NH(CH_2)_4NH(CH_2)_3NH_2-$ wherein m=1, 2, or 3; n=2, 3, 6, and o=3 or 4; and whereby a biomolecule is linked to the nanoparticle through the amino group.

In another aspect of the invention, there is provided a process for synthesizing an amine functionalized magnetic metal oxide nanoparticle via the steps of (i) obtaining a polymer having a plurality of carboxyl groups attached thereto, (ii) contacting the polymer with magnetic metal oxide to produce a coated magnetic metal oxide wherein a portion of said carboxyl groups are associated with the metal oxide; and (iii) reacting the coated magnetic metal oxide of step (ii) with a diamine. In one embodiment the diamine is ethylene diamine; in another embodiment the diamine is hexane diamine.

In another aspect of the invention, the contacting step in the synthesis further includes the steps of (a) providing a solution of soluble iron salts; (b) converting the iron salts into iron oxide crystals; and (c) removing unassociated polymer. In yet another aspect of the invention, the converting process includes the further steps of (a) heating the iron salts to a temperature between about 4° C. and about 20° C.; and adding an amount of base to raise the pH to about 8 or higher to form iron oxides. In another aspect, the process includes the step of heating the iron oxides to a temperature about 60° C. or more. for at least 30 minutes.

Another aspect of the invention provides a pharmaceutical composition of the nanoparticle biomolecule conjugates and a pharmaceutically acceptable carrier. This composition is particularly useful in targeted MR imaging applications.

BRIEF DESCRIPTION OF THE FIGURES

In all figures, the large sphere represents the core magnetic material.

In FIG. 2A, the prior art nanoparticles use crosslinked dextran and ammonia. This produces a functionalized particle in which every nitrogen is a primary amine. The polymer is associated with the magnetic core (large sphere) via hydroxyl groups.

In FIG. 2B, the prior art nanoparticles use non-crosslinked dextran which has been reacted with periodate to form aldehydes, followed with EDA and a reducing agent. There are two nitrogen atoms for every primary amine: a terminal amino group (1) linked to the polymer through methyl amine groups (the dashed box, showing second amine 2). There are no peptidyl linkages. The polymer is associated with the magnetic core (large sphere) via hydroxyl groups.

FIG. 2C shows the nanoparticles of the present invention. The polymer is noncrosslinked, and the amino group is linked to the polymer via a peptide bond. There are two nitrogen atoms for each primary amine: terminal amine 1 and at peptidyl linkage 2. The noncrosslinked polymer is associated with the magnetic core (large sphere) via carboxyl groups.

DETAILED DESCRIPTION

Figure 1:
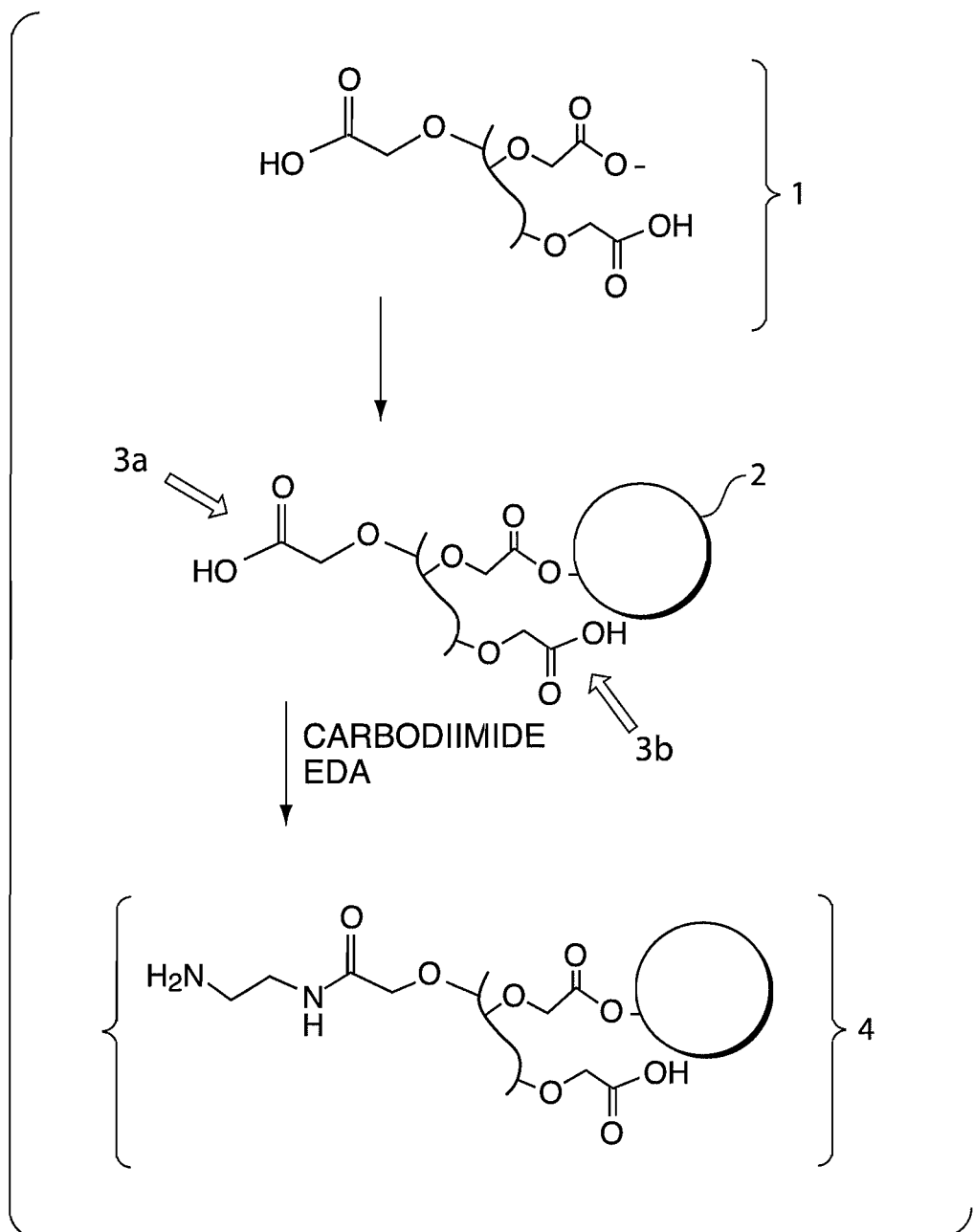
FIG. 1 shows a reaction scheme for synthesis of amino functionalized magnetic nanoparticles. First, a polymer 1 having multiple carboxyl groups is obtained. Next, the polymer is used to synthesize a coated nanoparticle. The core magnetic material is shown as a dark sphere 2. Carboxyl groups face (i) both the magnetic core which are blocked (arrow 3b) and (ii) the solvent (arrow 3a) and are available for further reaction. Third, the free carboxyl groups are reacted, here with carbodiimide, to produce the amine functionalized nanoparticle 4.

The present invention meets the aforementioned requirements by providing novel compositions of amino functionalized nanoparticles, and their methods of synthesis. These novel amino functionalized nanoparticles can serve further as magnetic nanoparticles for the development biomolecule-magnetic nanoparticle conjugates useful in a variety of in vitro, and in vivo applications.

Definitions

A nanoparticle as described and claimed herein is a material with a "core" of magnetic material associated with a polyfunctional noncrosslinked polymer. The polymer coating displays a plurality of carboxyl groups and reactive primary amino groups; a portion of the carboxyl groups are associated with the magnetic core; the reactive primary amino groups are available for subsequent covalent reactions, e.g., for the attachment of biomolecules. The nanoparticles have an overall size less than about 100 nm, before conjugation to biomolecules. The overall size of the nanoparticles is about 15 to 100 nm, preferably about 20 to 100 nm, more preferably about 40 to 60 nm; about 50 nm is the most preferred. The polymeric coating can be about 5 to 20 nm thick or more. Size can be determined by laser light scattering by atomic force microscopy or other suitable techniques.

The nanoparticle core can be monodisperse (a single crystal of a magnetic material, e.g., metal oxide, such as superparamagnetic iron oxide, per particle) or polydisperse (a plurality of crystals, e.g., 2, 3, or 4, per particle). The metal oxides are crystals of about 1-25 nm, preferably about 3-10 nm, and most preferably about 5 nm in diameter. The magnetic metal oxide can also comprise cobalt, magnesium, zinc, or mixtures of these metals with iron. The term "magnetic" as used in this specification and the accompanying claims means materials of high positive magnetic susceptibility.

In a preferred embodiment, a superparamagnetic form of iron oxide is used. Superparamagnetic iron oxide is one of the highly magnetic forms (magnetite, non-stoichiometric magnetite, gamma-ferric oxide) that has a magnetic moment of greater than about 30 EMU/gm Fe at 0.5 Tesla and about 300 K. When magnetic moment is measured over a range of field strengths, it shows magnetic saturation at high fields and lacks magnetic remanence when the field is removed.

The "polymer coating" is a natural or synthetic polymer associated with the magnetic core that functions to keep the metal oxides dispersed from each other. In one embodiment the polymer "coating" is not a continuous film around the magnetic metal oxide, but is a "mesh" or "cloud" of extended polymer chains attached to and surrounding the metal oxide. The polymer coating may be a natural polymer, a synthetic polymer. The polymer maybe linear, or moderately or highly branched. In one embodiment, the polymer coating can be carboxy dendrimers, commercially available from Sigma-Aldrich, which are highly branched polycarboxyl polymers. Other embodiments of the polymer coating are described in detail below.

A natural polymer is obtained when a pure polymer, such as a polysaccharide, is synthesized by a microorganism, plant or animal and extracted in substantially pure form. Non limiting examples of natural polymers include polysaccharides, such as dextran. A synthetic polymer is obtained from non-biological syntheses, by using standard polymer chemistry techniques known to those in the art to react monomers into polymers. The polymers may be homopolymers, i.e., synthesized from a single type of monomer, or co-polymers, i.e., synthesized from two or more types of monomers. Non-limiting examples of synthetic polymers include polymethylmethacrylate polymers and polyvinyl alcohol polymers.

A crosslinked polymer is one in which functional groups on a polymer chain and/or branches has reacted with functional groups on another polymer to form polymer networks. Crosslinked polymers are characterized herein as being heat stable and resistant to breakdown in biological systems. A crosslinked polymer has a molecular weight significantly higher than the original starting polymer.

A non-crosslinked polymer is described and claimed herein as a polymer in which few or no individual polymer chains have reacted with the functional groups of another polymer chain to form the interconnected polymer networks. A non-crosslinked polymer that has been functionalized is reasonably size homogeneous as compared to the starting polymer, i.e., the polymer before and after incorporation of amine and carboxyl functional groups have similar molecular weights and molecular weight distributions. A small increase in molecular weight of the polymer is seen generally as a result of the incorporation of functional groups onto the polymer and the few crosslinks that may occur on a statistical basis.

A polycarboxyl (or carboxyl) polymer is a polymer with more than one carboxyl group per polymer.

A polyfunctional polymer is one with different functional groups, such as amino and carboxyl groups attached to a polymer.

Description

We have surprisingly discovered that amino functionalized nanoparticles can be synthesized using non crosslinked, carboxylated polymers, and that these polymers permit the addition of reactive primary amine groups to the polymer. These reactive primary amines are attached to the polymer via peptidyl linkages.

When the noncrosslinked carboxylated polymers are used in the synthesis of the nanoparticles, the resulting polymer coated nanoparticle has two classes of carboxyl groups with very different chemical reactivities. Some carboxyl groups are shielded from further chemical reaction by forming a strong bond between the polymer and the surface of the iron oxide. Some surface carboxyl groups, facing the bulk solvent, can be activated with carbodiimide and converted to reactive primary amino groups (FIG. 1). These reactive primary amines can be reacted with bifunctional conjugating agents and then with biomolecules to form targeted MR contrast agents, or probes for used in biosensors.

As shown in FIG. 1, the process for synthesizing magnetic nanoparticles involves three general steps: (i) obtaining a polycarboxylated polymer; (ii) synthesizing a polycarboxylated coated magnetic nanoparticle; and (iii) converting the surface carboxyl groups to reactive primary amine groups while the remaining carboxyl groups bind the polymer to the nanoparticle (FIG. 1).

As a result of this procedure, the magnetic nanoparticles of the invention have polyfunctional polymeric coating, i.e. one that contains both amino and carboxyl groups. Since the carboxylated polymer used to synthesize the magnetic nanoparticle in step (ii) possesses only a single class of carboxyl groups, it is highly surprising that the resulting polymer coated magnetic nanoparticle consists of two distinct types of carboxyl groups. One type is bound to the surface of the iron oxide (blocked from further chemical reaction). A second type is exposed to the bulk solvent and available for conversion to reactive primary amino groups, see FIG. 1. Moreover, the chemistry used to incorporate the functional groups results in a polymer coating that is noncrosslinked (i.e., uncrosslinked or minimally crosslinked).

The presence of both reactive primary amino and carboxyl groups on the polymeric coating of the magnetic nanoparticles is one of the distinctive features of the invention. Polymers containing both reactive primary amino groups and carboxyl groups are difficult to develop because of the propensity for self-reaction. In solution at neutral pH, the positively charged carboxyl group and negatively charged amino group form non-covalent electrostatic bonds. When covalent modification of amino and carboxyl group containing polymers is attempted, activation of the carboxyl groups with a carbodiimide results in the formation of peptidyl bonds by reaction amino groups on the same molecule. This results in intrachain crosslinking when the reactive amino groups are on the same polymer, or interchain crosslinking when the amino group is on a second polymer molecule. Such interchain cross-linking can be induced in proteins, which present a mixture of amino and carboxyl groups on the surface, by activating agents like carbodiimide and is used to make aggregates of soluble proteins. For this reason the synthesis of polymers such as peptides containing amino and carboxyl groups requires use of protecting groups followed by deprotection. The synthesis used here eliminates the protection-deprotection reaction steps.

Another feature of the amine functionalized nanoparticles of the invention is that they can be readily degraded to yield their metal salts and polymer coating. In one embodiment, the degradation yields iron salts and the polyfunctional polymeric coating. In vivo, this results in the utilization of iron oxide, by incorporation of iron into red blood cells, and by the excretion and/or degradation of the polycarboxylated polymer. In vitro, the conditions of biodegradation can be simulated by exposing nanoparticles to mildly acidic pH (3-6) in the presence of a metal chelator, e.g. citrate or EDTA. This yields ferric ion chelates and soluble polyfunctional polymers. The molecular weight of the polyfunctional polymers, bearing amino and carboxyl groups, will be slightly larger than the polycarboxylated polymers used to synthesize the nanoparticles due the addition of reactive primary amino groups.

The amine functionalized nanoparticles of the invention are synthesized by activation of free carboxyl groups of the nanoparticle with a water soluble carbodiimide, followed by reaction with a large excess of a diamine. The nature of the diamine provides a linker arm of varying lengths and chemistries for the attachment of biomolecules. Nonlimiting examples of diamines include ethylenediamine (EDA), propyldiamine, spermidine, spermine, hexanediamine, and diamine amino acids, such as lysine or ornithine.

Figure 2A:
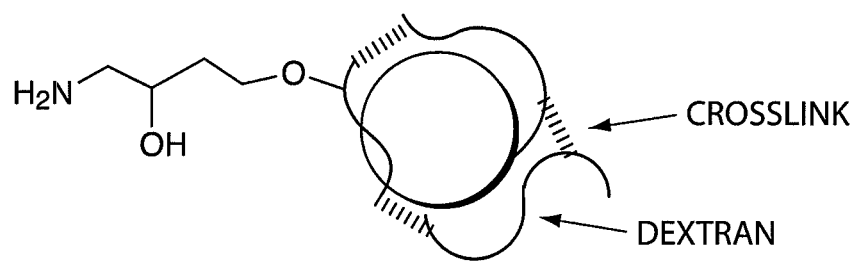
FIGS. 2A-C are comparisons of the prior art nanoparticles (FIGS. 2A and 2B) with the nanoparticles of the invention (2C).

Unlike the synthesis for other amine functionalized particles, ammonia is not used to make the amine functionalized nanoparticles of the invention. For example, in the synthesis of amino-CLIO, dextran coated magnetic nanoparticles are reacted with epichlorohydrin, followed by reaction with ammonia. This reaction produces a dextran crosslinked, amine functionalized nanoparticle bearing primary amino groups ($H_2N-CH_2-CHOH-CH_2-O-$ Polymer), as shown in FIG. 2A. If the carbodiimide activated carboxylated nanoparticles of this invention were reacted with ammonia, an amide would be obtained ($H_2N-CO-CH_2-O-$ Polymer). The nitrogen atoms of amides are far less reactive than primary amino groups and not satisfactory for reaction with the bifunctional conjugating reagents used to attach biomolecules.

The reaction with diamine is performed under conditions that prevent crosslinking between nanoparticles. This is accomplished by using a large excess of diamine. In general the moles of diamine used will exceed the number of carboxyl groups present by a factor of at least 10. Diamines are cheap and can be used in very large excess. Unreacted diamine (MW<2 kDa) can be separated from amino functionalized nanoparticle (MW>500 kDa) by ultrafiltration. Alternatives to ultrafiltration for the removal of unreacted diamine include gel permeation chromatography, dialysis, and precipitation and resolubilization of the nanoparticle.

Figure 2B:
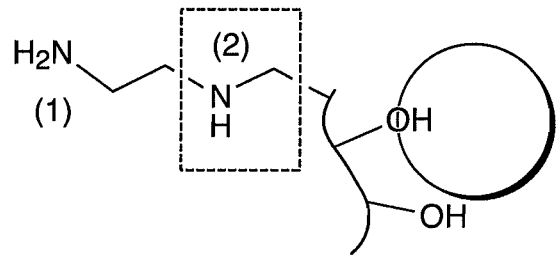

When the carbodiimide activated carboxylated nanoparticles of the invention are reacted with a large excess of diamine, one of the nitrogen atoms reacts with the carboxyl group to provide a peptide bond, while a second exists as a primary amine suitable for further chemistry. Hence the amino functionalized nanoparticles of the invention have a characteristic general structure that includes a peptidyl bond and a primary amino group, see FIGS. 1 and 2C. This characteristic structure is not found with amino functionalized amino-CLIO nanoparticle. Similarly, a peptide bond is not obtained when dextran coated magnetic iron oxides are activated by treatment with periodate, followed by reaction with a primary amine and treatment with a reducing agent. In this case a methyl amine linkage is obtained (FIG. 2B).

The presence of primary amino groups on the magnetic nanoparticles can be readily ascertained by reaction with amine specific reagents such as TNBS or ninhydrin or SPDP with the in tact magnetic nanoparticle. Since the carboxyl groups are protected by the metal oxide, they can be most easily analyzed after digestion of the metal oxide core and isolation of the polymeric coating. Digestion of metal oxide core can be accomplished by treatment with acid and chelator. Typically a pH below 5, or between 2 and 5, is sufficient. Chelators like citrate or EDTA enhance the solubility of iron and are added an amount sufficient to bind all metal ions. After digestion, the metal is removed by passage over a cation exchange column or metal removing chelating column such as Chelex. The polymer is then analyzed by IR and shows characteristic peaks from carboxyl groups. Polymers with carboxyl groups have characteristic absorption frequencies from the carbonyl group (C=O) of the carboxyl (1780 to 1710 cm-1, strong) and the hydroxyl group (3000 to 2500 cm-1, broad, variable).

The polymer obtained after digestion and removal of iron can also be characterized by size and compared with the polymer used in the nanoparticle synthesis. The polymer will be slightly larger than the starting polymer due to addition of amino groups.

Figure 2C:
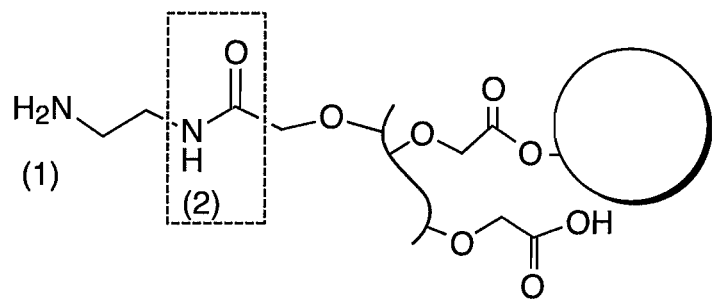

A second property of the amine functionalized polymers of the invention is presence of at least two nitrogen atoms for each primary amine due to characteristic general structure ($H_2N-X-NH-CO-$), see also FIG. 2C. X can be any structure connecting the two primary amines of the diamine. Non limiting examples include hexamine diamine, ethylene diamine, spermidine or spermine, and amino acids like ornithine or lysine, which are of interest because of their negatively charged carboxyl group. The total number of nitrogen groups attached to the purified polymer can be obtained by submitting the purified polymer to elemental analysis of nitrogen, i.e., determination of the content of all nitrogen atoms. The number of reactive primary amino groups can be determined by the TNBS method. A property of the amine functionalized polymers of the invention is the amount of total nitrogen will exceed the amount of nitrogen present as a primary amine. For example, when ethylene diamine (EDA) has been used, the total nitrogen content will be twice the nitrogen content obtained with methods determining the amount of primary amine.

Properties and sources of polycarboxylated polymers for the synthesis of coated nanoparticle. The polycarboxylated polymers can be obtained by a variety of routes and have a variety of compositions. They may be man made or naturally occurring and may be highly branched or linear.

The polycarboxylated polymers have a molecular weight between about 5 and 200 kDa, more preferably between 5 and 50 kDa. Smaller polymers lack a sufficient number of carboxyl groups to both strongly bind to the iron oxide and have the numerous free carboxyl groups available for conversion to amino groups (FIG. 1). The polymers must contain more than about five moles of carboxyl group per mole of polymer. The number of carboxyl groups can be determined by titration. The polycarboxylated polymers should have a high water solubility over a wide range of pH's to be employed in the synthesis of water soluble polymer coated magnetic nanoparticles.

To be used in the synthesis of polymer coated magnetic nanoparticles, unreacted polymer must be separated from polymer coated nanoparticle. To do this easily and efficiently, it is preferred that the polymer maintain a homogenous size distribution, which can be determined by the usual methods of polymer chemistry including light scattering, gel permeation chromatography. For example, unreacted carboxymethylated dextran (MW=20 kDa) can be readily separated from the coated nanoparticle (MW>500 kDa) by ultrafiltration using a membrane with a cutoff of 100 kDa (Groman WO 00/61191). Polymers larger than about 200 kDa can used but they are more difficult and more expensive to separate from the polymer coated nanoparticles as the larger molecular weight polymers and the polymer coated nanoparticles pass through the same membrane.

A preferred method of synthesizing polycarboxylated polymers is the reaction of a water soluble polymer containing multiple amino or hydroxyl groups with an alkyl halogenated acid in aqueous strong base. This method has several advantages. First, the size and size distribution of the polymer obtained will be determined the size of the starting polymer. Hence by selecting a size homogeneous polymer, the size homogeneity of the carboxylated polymer is achieved. The size of the polycarboxylated polymer will be slightly larger than the starting polymer due to the addition of carboxyl groups. For details see examples 1, 4 and 6, of Josephson et al WO97/21452. Second, polymers with varying number of carboxyl groups on them can be synthesized by varying the amount of halogenated acid, to determine the optimum level of carboxylation required for the synthesis of polymer coated magnetic nanoparticle, see Groman WO 00/61191. An alternative method is the direct synthesis of polycarboxylic functional polymers, such as polymethacrylic acid based polymers.

Naturally occurring hydroxylated polymers that can be used in the synthesis of polycarboxylated polymers include polysaccharides like dextran, starch or cellulose. Polyvinyl alcohol is a synthetic hydroxylated polymer that can replace naturally occurring polysaccharides. These hydroxyl group-bearing polymers are reacted with halogenated acids like bromoacetic acid, chloroacetic acid, bromohexanoic acid and chlorohexanoic acid in the present of strong base, typically 1-8 M NaOH. The polycarboxylated polymer is then purified by ultrafiltration or by precipitation. Alternatively anhydrides like succinic anhydride can be used for carboxylation polyhydroxylated polymers, but these result in ester linkages which can undergo slow hydrolysis.

Reaction of positively charged polymers like polylysine or poly vinyl amine with an anhydride (succinic anhydride, maleic anhydride, DTPA anhydride) provide another method of synthesizing carboxylated polymers.

Hydrolysis of an anhydride containing polymer, such as polytheyelene-alt-maleic anhydride (Sigma) is another method that can yield a suitable carboxylated polymer.

Carboxyl group bearing polyamino acids can also be employed as polycarboxylated polymers., e.g. polyaspartate or polyglutamate. Carboxylated dendrimers are available commercially and are highly branched synthetic polymers and can be used in the synthesis of nanoparticles.

Synthesis of Carboxyl Terminated, Polymer Coated Nanoparticles.

Carboxy terminated nanoparticles can be synthesized by mixing the carboxyl terminated polymer with ferrous and ferric salts. Metals other than iron can be used in the synthesis of magnetic metal oxides. For example, zinc, manganese or cobalt can partially or completely replace the ferrous ion during the synthesis of magnetic metal oxides.

The mixture is enclosed in a jacked reactor for temperature control and stirred. It is covered to control access of oxygen. The mixture is then brought to controlled temperature between 4 and 20 C, and a base, such as ammonia, is added. Base is added in a highly controlled fashion, either by pumping or by drop wise addition. Sufficient base is added to bring the pH to higher than pH 8, which causes the formation of iron oxides. The resulting gel or colloid maybe heated, to induce formation of the highly magnetic iron oxide. The temperature of the mixture is heated to above 60 C for more than 30 minutes. Finally, the colloid is allowed to cool and unreacted polymer removed from the polymer coated nanoparticle. The preferred technique for removal is ultrafiltration, using a membrane that has a cutoff that permits the carboxylated polymer to pass through, while the larger coated nanoparticle is retained. Alternatives to ultrafiltration are gel filtration and magnetic separation. Citrate maybe added as stabilizer but it must be removed by ultrafiltration before use of carbodiimide because of its carboxyl groups. Details methods for the synthesis of polycarboxylated polymer coated nanoparticles can be found in Groman and Manro Synthesis of Amine Terminated, Polymer Coated Nanoparticles.

The carboxyl groups of the carboxyl terminated nanoparticle are then activated by the use of a water soluble carbodiimide. Typically this is done in a non-amine containing buffer between pH 4.5 and 7. The activation with 0.1 M TEMED, pH 4.8 has been found to satisfactory. Activation is typically done at 20-40 C. EDA) is added in vast excess to prevent the formation of crosslinks between the carboxyl groups. Excess diamine can be separated from the aminated, polymer coated nanoparticle using ultrafiltration. The use of carbodiimide results in the formation of a peptide bond between the diamine linker and polymeric nanoparticle coating. The number of primary amines on the particle can be monitored by reaction with trinitrobenze. A variety of diamines can be used such as hexamine diamine, ethylene diamine, spermidine or spermine. Amino acids like ornithine or lysine are diamines of interest because of their negatively charged carboxyl group.

The aminofunctionalized nanoparticles can be used as attachment substrates to form a variety of nanoparticle conjugates for in vivo or in vitro applications. Example applications include cell sorting, in vitro assays and in vivo applications such as magnetic resonance imaging. A non limiting exemplary conjugate is a biomolecule nanoparticle conjugate.

The amino terminated nanoparticle is then reacted with a bifunctional conjugation reagent designed to react with amino groups. Preferred conjugation reagents are NHS esters, which react with the amine group of the nanoparticle, and which have second moiety that can react with the sulfhydryl group of the biomolecule. Such crosslinking agents include, for example, SPDP, long chain-SPDP, SIA, MBS, SMCC, and others that are well known in the art and are available from Piece Chemical Company. Detailed procedures for their are available from the Piece Chemical web site, see http://www.piercenet.com/ and the attached pdf files downloaded from that site.

The activated biomolecule, preferably with a single sulfhydryl group distal from the site of bioactivity, is allowed to react with the activated nanoparticle. Separation of unreacted biomolecule from the biomolecule-nanoparticle conjugates can be accomplished by gel filtration, ultrafiltration, dialysis or magnetic separation methods. Examples of thiolated biomolecules that have been attached to SPDP activated crosslinked magnetic nanoparticles include transferrin, (Hogemann, (2000) *Bioconjug Chem* 11, 941-6), tat peptides (Josephson, (1999) *Bioconjug Chem* 10, 186-91; Zhao (2002) *Bioconjug Chem* 13, 840-4), oligonucleotides (Josephson (2001) *Agnew Chem Int Ed* 40, 3204-3206; Perez, (2002) *J Am Chem Soc* 124, 2856-7), antibodies (Kang, (2002) *Bioconjug Chem* 13, 122-7) and proteins (Perez, *Nature Biotechnol* 20, 816-20). For peptides (1-2 kDa), 5-25 peptides can be attached per 2000 Fe atoms. For proteins, such as transferrin or antibodies (50-200 kDa) 1-4 biomolecules can be attached per 2000 Fe atoms.

Uses of the Biomolecule-Nanoparticle Conjugates

The magnetic nanoparticles of the invention have various uses with in vitro ligand binding assays. The nanoparticles can be used in magnetic detection based assays (see Simmonds U.S. Pat. Nos. 6,046,585 and 6,275,031, Rohr U.S. Pat. No. 5,445,970; Ebersole, U.S. Pat. No. 4,219,335, Chemla, et. al. (2000) Ultrasensitive magnetic biosensor for homogeneous immunoassay. *Proc Natl Acad Sci USA* 97, 14268-72). They can also be used in magnetic resonance based ligand binding assays such as Josephson U.S. Pat. No. 5,164,297 and Perez et al *Nature Biotechnol.* 2002 August; 20(8):816-20.

The magnetic nanoparticles of the invention of the invention are also suitable for cell sorting applications. Magnetic nanoparticles were described by Molday U.S. Pat. No. 4,452,773 and commercially available (Miltenyi Biotech, Auburn, Calif., and Molecular Probes, Eugene, Oreg.).

Finally the magnetic nanoparticles of the invention can be used as for targeted MR imaging applications.

For in vivo uses, the biomolecule-nanoparticle conjugates are formulated and sterilized according to the published methods for sterilizing parenterally administered MRI contrast agents. For parenteral applications, sterilization can be achieved by filtering the colloid through a 220 nm filter (filter sterilization) or by heat sterilization (terminal sterilization). Depending on the method of sterilization various excipients, such as monosaccharides, polysaccharides, salts, can be added to stabilize the colloid during heat stress or storage. Excipients can also serve to bring the ionic strength and pH of the preparation into the physiological range. See Josephson U.S. Pat. No. 5,160,726, Groman U.S. Pat. No. 5,248,492.

EXAMPLES

Example 1

Synthesis of a Carboxymethylated Polyhydroxylated Polymer

Carboxymethylated polymers are prepared by reaction of a halo acetic acid with a polymer in strong base, usually NaOH. The polymer should be of sufficient molecular weight to allow separation from unreacted haloacetic acid from the carboxymethylated polymer. The polymer is preferably between 5 kDa and 100 kDa. The separation can be accomplished by dialysis, ultrafiltration or precipitation. The polymer is then dried by lyophilization, vacuum drying or spray drying. The polymer should be of sufficient molecular weight to allow separation of dextran from dextran coated iron oxide. For example, when the nanoparticles have molecular weights of greater than 500 kDa, and the polymer is preferably less than 100 kDa, this separation can be accomplished by ultrafiltration.

(Poly)vinyl alcohol (100 g, MW=15 kDa) was dissolved in 1000 ml of hot water. After reaching room temperature, 600 ml of 8M NaOH solution was added to it with stirring and again equilibrates to room temperature. 100 g of bromoacetic acid was then added and mixture stirred for two hours. The polymer was neutralized with 6M HCL. It was then dried under vacuum overnight at room temperature. It is denoted CM-PVA.

Example 2

Synthesis of Carboxymethylated Polymer Coated Nanoparticle

One hundred milliliters of a solution of 12 mmoles of ferric chloride (hexahydrate) and 6 grams of CM-PVA. was prepared. The solution was filtered and cooled to 2-4 C. To the mixture was added 6 mmoles of ferrous chloride (tetrahydrate) dissolved in 5 mL of water. While being stirred rapidly, 4.5 mLs of 28-30% ammonium hydroxide (2-4 C) was added dropwise. The mixture was then heated to between 70 and 90 C and maintained at the higher temperature for 2 hours. Unreacted CM-PVA was removed by ultrafiltration using a 100 kDa cutoff membrane. The colloid had a size of 54 nm by light scattering and an R2 of 60 mM−1 sec−1. The procedure was repeated using 3 g CM-PVA to give a colloid with 65 nm and an R2 of 160 mM−1 sec−1.

Example 3

Conversion of Carboxyl Groups on the Magnetic Nanoparticle to Amino Groups

To 10 mLs of 10 mg Fe/mL of the carboxylated polymer coated nanoparticle in 0.1 M TEMED buffer, pH 4.8, was added 0.2 g of 1-ethyl-3-(dimethylaminopropyl) carbodiimide hydrochloride at room temperature. After 15 minutes, 0.5 mL 1,2 ethylene diamine was added. After 24 hours the mixture was put in dialysis bag and dialyzed until the dialysate was free of amine by the TNBS assay.

Example 4

Reaction of Amino-Functionalized Magnetic Nanoparticles with a Biomolecule

Nanoparticles were reacted with N-succinimidyl 3-(2-pyridyldithio)propionate (SPDP). To 1 mL of amino functionalized magnetic nanoparticle (10 mg Fe) was added 1 mL of 0.1 M phosphate buffer, pH 7.4, and 2 mL of 25 mM SPDP in DMSO (50 umoles SPDP). The mixture was allowed to stand for 60 min at room temperature. Low molecular impurities were removed by PD-10 columns (Sigma Chemical, St. Louis, Mo.) equilibrated with 0.01M Tris and 0.02M citrate, pH 7.4 buffer. The number of amine groups can be obtained for the amount of 2PT released assayed by addition of dithiothreitol. (Zhao, (2002) Bioconjug Chem 13, 840-4).

It will be apparent to those skilled in the art that other changes and modifications may be made in the above-described compounds, compositions, and methods for making and using the same, without departing from the scope of the invention herein, and it is intended that all matter contained in the above description shall be interpreted in an illustrative and not in a limiting sense.

We claim:

1. A nanoparticle comprising: a magnetic core of one or more metal oxide crystals; and a carboxymethyl-polyvinyl alcohol polymer coating associated with the core through a plurality of carboxyl groups, wherein the nanoparticle further comprises one or more reactive amino groups each attached to the polymer coating via an amide linkage.

2. The nanoparticle of claim 1, wherein reactive amino groups are associated with the polymer coating through a linkage of the formula:

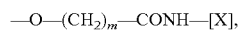

—O—(CH$_2$)$_m$—CONH—[X], wherein X is $-(CH_2)_nNH_2$, $-(CH_2)_3NH(CH_2)_4NH_2$ or $-(CH_2)_3NH(CH_2)_4NH(CH_2)_3NH_2$; wherein m=1, 2, or 3 and n=2-6.

3. The nanoparticle of claim 1, wherein the magnetic core comprises one or more superparamagnetic iron oxide crystals.

4. The nanoparticle of claim 1, wherein the magnetic core has a diameter between about 1 nm and about 25 nm.

5. The nanoparticle of claim 1, wherein the nanoparticle has a diameter between about 15 nm and about 100 nm.

6. The nanoparticle of claim 1, further comprising one or more biomolecules.

7. The nanoparticle of claim 6, wherein the biomolecule is selected from the group consisting of a peptide, protein, antibody and oligonucleotide.

8. The nanoparticle of claim 1, wherein the polymer comprises more than five moles of carboxyl groups per mole of polymer.

* * * * *